US006468531B1

(12) United States Patent
Matthew et al.

(10) Patent No.: US 6,468,531 B1
(45) Date of Patent: Oct. 22, 2002

(54) METHOD OF PROMOTING CELLULAR FUNCTION

(75) Inventors: William D. Matthew; Marcia J. Riggott, both of Durham, NC (US); Eva S. Anton, Hamden, CT (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 08/303,026

(22) Filed: Sep. 8, 1994

Related U.S. Application Data

(63) Continuation-in-part of application No. 08/123,851, filed on Sep. 9, 1993, now abandoned.

(51) Int. Cl.[7] ...................... A61K 39/395; A61K 39/00; C07K 16/28
(52) U.S. Cl. ................ 424/143.1; 424/131.1; 424/133.1; 424/141.1; 424/152.1; 424/172.1; 530/387.2; 530/387.3; 530/388.2; 530/388.22; 530/388.9; 530/389.1
(58) Field of Search .................. 424/131.1, 133.1, 424/141.1, 143.1, 152.1, 172.1, 175.1; 435/240.1, 327, 334, 345; 530/387.2, 387.3, 388.2, 388.22, 388.9, 389.1

(56) References Cited

U.S. PATENT DOCUMENTS

| | | | | | |
|---|---|---|---|---|---|
| 4,699,880 A | * | 10/1987 | Goldstein | ................ | 435/172.2 |
| 4,849,413 A | * | 7/1989 | della Valle et al. | ........... | 514/54 |
| 5,144,010 A | * | 9/1992 | Erlanger et al. | ......... | 530/387.2 |
| 5,279,966 A | * | 1/1994 | Jessell et al. | ............ | 435/320.1 |

OTHER PUBLICATIONS

Goldstein et al., Scientific Amer, 255:74–83, 1986.*
T.M. Jessell, "Reactions of Neurons to Injury", from: "Principles of Neural Science Third Edition", Ed. E.R. Kandel et al., Elsevier, 1991, pp. 258–269.*
Borrebaeck et al., Imm. Today, 14:477–479, 1997.*
Edgington, Bio/Technology, 10:383–386, 388, 389, 1992.*
Waldmann, Science, 252:1657–1662, 1991.*
Harris et al., Tibtech, 11:42–44.*
Guillet et al., PNAS, 82:1781–84, 1985.*
Bradley, Chapter 10, pp. 235–238, from: "Selected Methods in Cellular Immunology", ed. B. B. Mishell et al., W. H. Freeman and Co., 1980.*
Bailey et al, "The influence of fibronectin and laminin during Schwann cell migration and peripheral nerve regeneration through silicon chambers", Journal of Neurocytology 22:176 (1993).

Lundborg et al, "Nerve Regeneration in Silicone Chambers: Influence of Gap Length and of Distal Stump Components", Experimental Neurology 76:361 (1982).
Lungborg et al, "In Vivo Regeneration of Cut Nerves Encased in Silicone Tubes", Journal of Neuropathology and Experimental Neurology 41(4):412 (1982).
Neugebauer et al, "Cell–surface regulation of $\beta_1$–integrin activity on developing retinal neurons", Nature 350:68 (1991).
Boucheix et al, "Characteristics of platelet aggregation induced by the monoclonal antibody $ALB_6$ (acute lymphoblastic leukemia antigen p 24)" FEBS 161(2):289 (1983).
Griffith et al, "Platelet Activation by Immobilized Monoclonal Antibody: Evidence for a CD9 Proximal Signal", Blood 78(7):1753 (1991).
Matthew et al, "Cyclophosphamide treatment used to manipulate the immune response for the production of monoclonal antibodies", Journal of Immunological Methods 100:73 (1987).
"Science and Business", Scientific American pp. 101–103, Jul. 1993.
Sharon et al, "Carbohydrates in Cell Recognition", Scientific American pp. 82–89, Jan. 1993.
The Genesis Report™ /Rx, "Business Implications of Technology Innovation in Pharmaceuticals" 1(2):1–3 (1992).
Hodgson, "Carbohydrate–Based Therapeutics", Bio/Technology 9:609 (1991).
Schreiber et al, Proc. Natl. Acad. Sci. USA 78(12):7535–7539 (1981).
Sege et al, Proc. Natl. Acad. Sci. USA 75(5):2443–2447 (1978).
Haynes et al, Int. J. Dev. Neurosci. 7(6):623–632 (1989) (Abstract thereof).
Buttke et al, "Oxidative stress as a mediator of apoptosis", Immunol. Today 15:7–10 (1994).
Deng et al, "Amyotrophic Lateral Sclerosis and Structural Defects in Cu,Zn Superoxide Dismutase", Science 261:1047–1051 (1993).
Coyle et al, "Oxidative Stress, Glutamate, and Neurodegenerative Disorders", Science 262:689–695 (1993).

* cited by examiner

Primary Examiner—Ronald B. Schwadron
(74) Attorney, Agent, or Firm—Nixon & Vanderhye P.C.

(57) ABSTRACT

The present invention relates, in general, to a method of producing a therapeutic effect and, in particular, to a method of using antibodies to promote cellular function, to antibodies suitable for use in such a method and to compositions comprising same.

4 Claims, 10 Drawing Sheets

METHOD OF PROMOTING CELLULAR FUNCTION

This application is a continuation-in-part of Application No. 08/123,851, filed Sep. 9, 1993, now abandoned the entire contents of which are incorporated herein by reference.

This invention was made with Government support under Grant No. BNS-90-06752 awarded by the National Science Foundation. The Government has certain rights in the invention.

TECHNICAL FIELD

The present invention relates, in general, to a method of producing a therapeutic effect and, in particular, to a method of using antibodies to promote cellular function, to antibodies suitable for use in such a method and to compositions comprising same.

BACKGROUND

To date, the use of immunoglobulins for therapy has been guided by the premise that antibodies neutralize antigens and block function or that antibodies can kill cells. The use of immunoglobulins for such purposes is well grounded in practice and research. Immunological therapies have been used to treat malignant tumors (Miller et al, New Eng. J. Med. 9:517 (1982)), to reduce allograft rejection (Bluestone et al, Immunol. Rev. 90:5 (1986)), and to prepare vaccines against viral infections (Finberg and Ertl, Immunol. Rev. 90:129 (1986)). The feasibility of using antibodies as therapeutics has been greatly improved by the development of technology to humanize rodent monoclonal antibodies and thereby render them non-immunogenic in humans (Hardman et al, J. Biol. Markers 7:203 (1992); Carter et al, Proc. Natl. Acad. Sci. USA 89:4285 (1992); Routledge et al, Eur. J. Immunol. 21:2717 (1991); Gussow and Seemann Meth. Enzyme 203:99 (1991)). Although humanized antibodies have certain side effects, such effects can generally be kept at therapeutically acceptable levels.

In contrast to the traditional use of immunoglobulins as agents to inhibit or neutralize function, the present invention is based on the realization that immunoglobulins can also be used as agonists to facilitate function. Neugebauer et al (Nature 350:68 (1991) disclose anantibody that promotes adhesion but no reference is made to inducing cell signalling or facilitating a cellular function, such as motility). Antibodies suitable for use in the present invention, designated "agonist antibodies", include those that are mirror images of a particular epitope. One method of generating such antibodies involves the manipulation of the immune system so as to prevent the normal suppression of the system that is responsible for preventing auto-immunity (Matthew & Sandrock, J. Immunol. Methods 100:73 (1987)). The immune system can thus be permitted to produce idiotypic antibodies that are directed to the original antigen and anti-idiotypic antibodies that are directed to the newly circulating antibodies (Jerne, Ann. Immunol. 125C:373 (1974); Matthew, Soc. for Neurosci. Short Course, Anaheim, Calif. (1992)). Anti-idiotypic antibodies can thereby be produced that mimic molecules (e.g. growth factors) that interact with cell surface receptors. In accordance with the present invention, such antibodies can be used as therapeutics to replace or supplement biologically active molecules in facilitating biological function.

OBJECTS AND SUMMARY OF THE INVENTION

It is a general object of the invention to provide antibodies that promote cellular functions such as survival, growth and motility.

It is a specific object of the invention to provide antibodies that mimic molecules that interact with cell surface receptors and thereby facilitate cellular functions.

It is another object of the invention to provide antibodies for use in promoting neuronal cell growth and glial migration.

It is a further object of the invention to provide methods of treating injuries and diseases, particularly those of the peripheral and central nervous system.

In one embodiment, the present invention relates to a method of facilitating a biological function of a cell. The method comprises contacting the cell with an antibody, or binding fragment thereof, that mimics an agent that binds to a receptor on the surface of the cell and thereby facilitates the function. The contacting is effected under conditions such that the antibody binds to the receptor and thereby facilitates the function.

In another embodiment, the present invention relates to a method of stimulating migration of a Schwann cell. The method comprises contacting the cell with an antibody, or binding fragment thereof, that binds to a receptor on the surface of the cell that regulates migration of the cell. The contacting is effected under conditions such that the antibody binds to the receptor so that migration is thereby stimulated.

In a further embodiment, the present invention relates to a method of treating a de-myelinating disease. The method comprises administering to a patient in need thereof an antibody, or binding fragment thereof, that binds to a receptor on the surface of Schwann cells of the patient that regulates migration of the Schwann cells. The amount administered is sufficient to stimulate migration of the Schwann cells.

In yet another embodiment, the present invention relates to a method of regulating calcium homeostasis of a mammal in need thereof. The method comprises administering to the mammal an amount of a GM1 anti-idiotypic antibody sufficient to effect the regulation.

In further embodiments, the present invention relates to an isolated GM1 anti-idiotypic antibody and an isolated antibody specific for a Schwann cell surface antigen that potentiates Schwann cell migration.

In yet another, embodiment, the present invention relates to a method of protecting a mammalian cell from a toxic effect of a free radical. The method comprises contacting the cell with an anti-idiotypic GM1 antibody under conditions such that the protection is effected.

Further objects and advantages of the present invention will be clear from the Description that follows.

DETAILED DESCRIPTION OF THE INVENTION

The present invention relates to a method of inducing a therapeutic effect in an animal, for example, a mammal, and derives from the realization that antibodies can be used to facilitate, rather than inhibit or block, the biological functions necessary for achieving the effect sought. Key to at least one embodiment of the present invention are the facts that growth factors and other biological molecules that interact with cell surface receptors can be mimicked by antibodies and that such antibodies can be used in therapy to replace or supplement the biologically active molecule that they mimic. The present invention thus relates to a novel method of using immunoglobulins as agonists. In view of the immense potential of the mammalian immune system to produce immunoglobulins (more than 100 million being possible), the invention should find application in virtually all fields of medical science.

Figure 1:
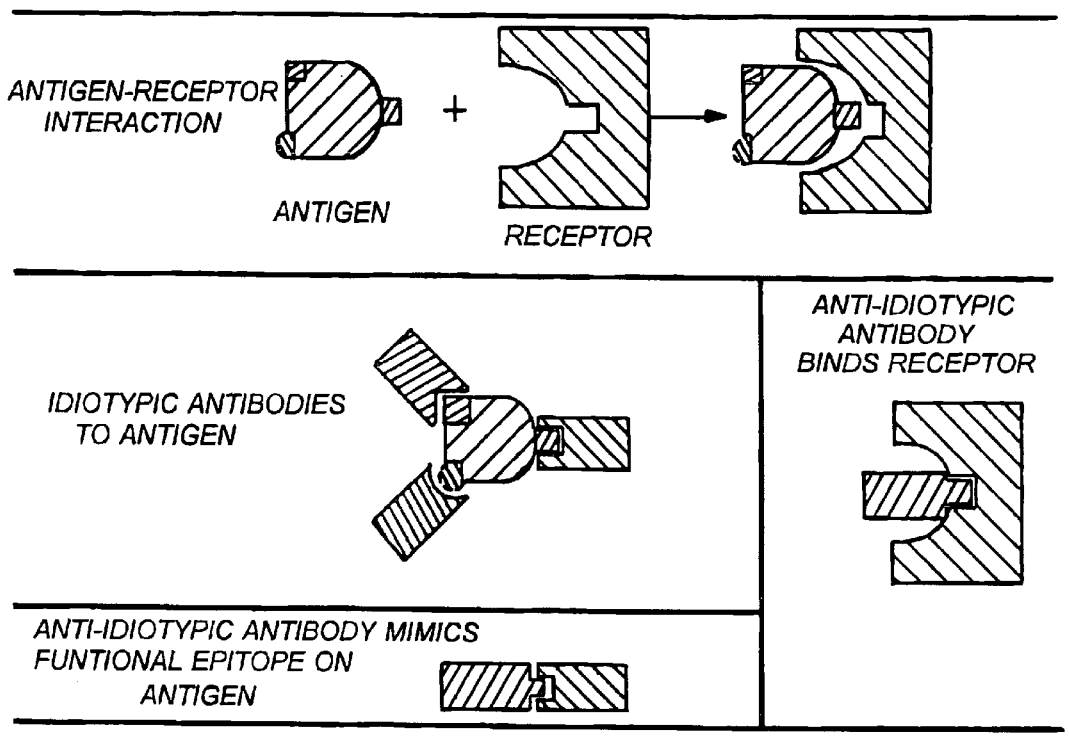
FIG. 1: Anti-idiotypic antibodies share structural homology with the antigen and can bind the functional sites of antigen receptors.
Figure 2A:
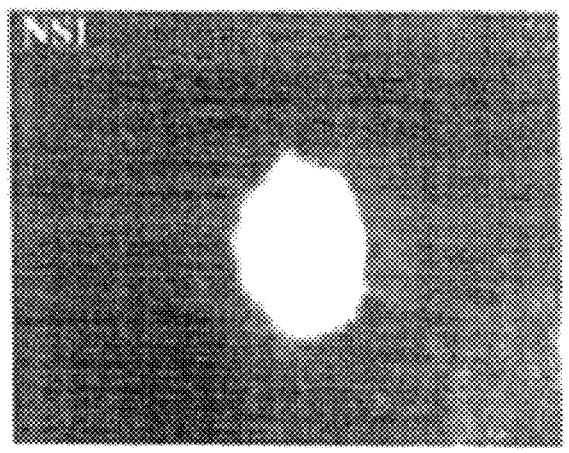
FIGS. 2A and 2B: Embryonic day 18 hippocampal cells were grown on normal sciatic nerve tissue sections. Cells grown in NS1 conditioned medium do not adhere to the tissue section but remain as unattached aggregates. In the presence of antibody 4, cells adhere to and extend processes on the nerve substrate.
Figure 2B:
Figure 3A:
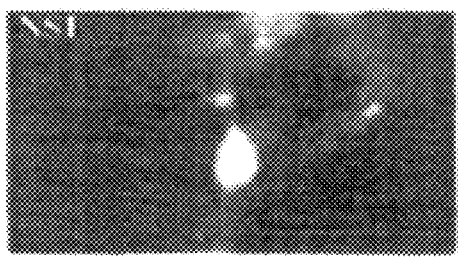
FIGS. 3A–3E: Embryonic day 18 hippocampal cells were grown on CELL-TAK (Collaborative Biomedical) in the presence of NS1 conditioned medium or antibodies. Although cells adhered in all cases, neurite outgrowth was strongly facilitated by the anti-idiotypic antibodies to GM1.
Figure 3B:
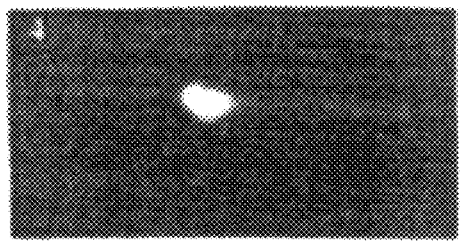
Figure 3C:
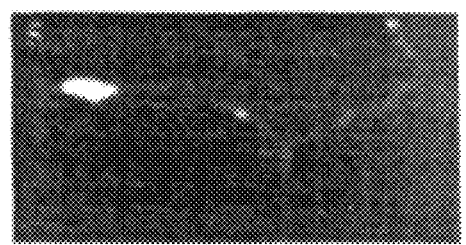
Figure 3D:
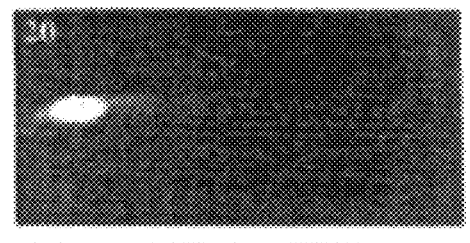
Figure 3E:
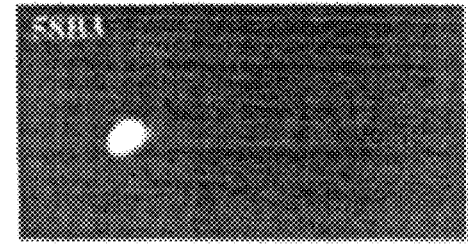
Figure 4:
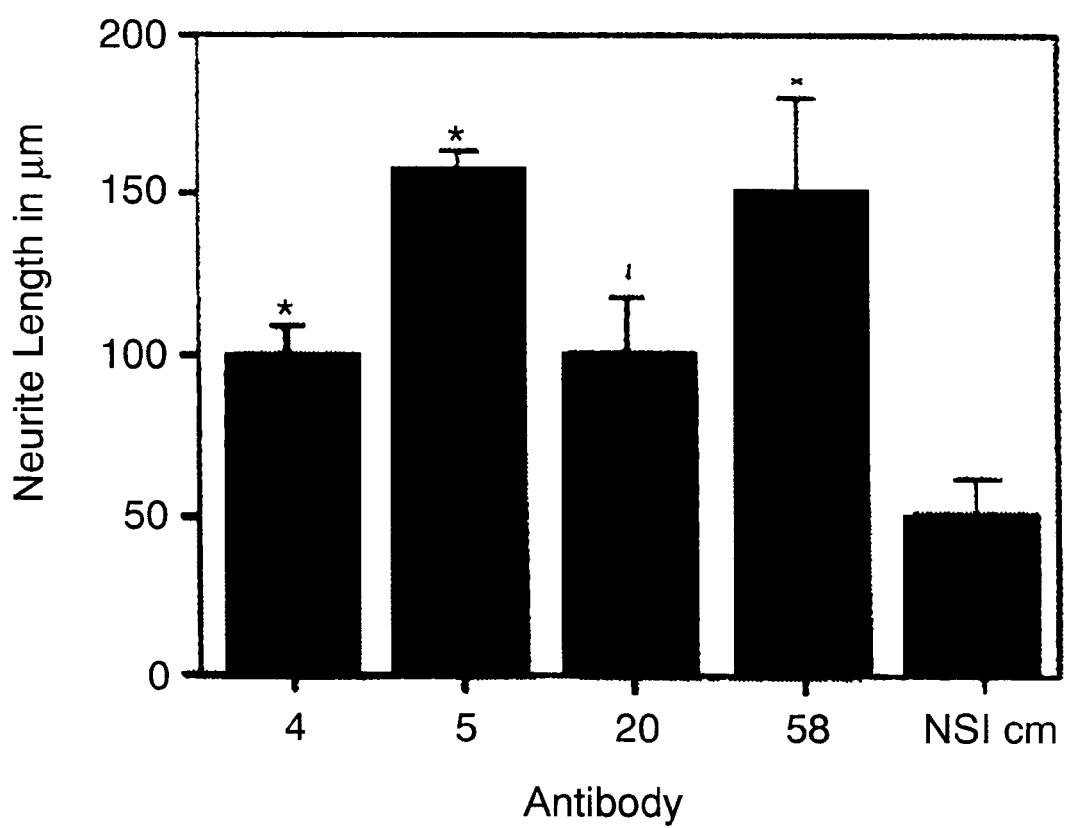
FIG. 4: Images obtained from hippocampal neurons grown on CELL-TAK (as described below with reference to FIG. 3) were collected on the IMAGE 1 system. The neurite lengths were traced and measured for 35 neurons. The mean ± standard deviation of neurite length is indicated for neurons grown in the presence of antibodies 4, 5, 20 and 58 or NS1 conditioned medium. The neuritic length for neurons grown in the presence of NS1 conditioned medium was significantly different from those grown in the presence of anti-idiotypic antibodies to GM1. Statistical significance was tested using a two-tailed t-test assuming equal variance at $P<0.05$.

Antibodies suitable for use in the present invention include anti-idiotypic antibodies, that is, antibodies that recognize the binding site of another antibody, the idiotype. An anti-idiotype, which is complementary to the idiotypic binding site, has structural homology to the original epitope on the antigen against which the idiotype is raised (FIG. 1).

The present invention results, at least in part, from the observation that anti-idiotypic monoclonal antibodies to the ganglioside GM1 are capable of inducing effects that mimic those associated with GM1. GM1 is known to enhance neuronal survival and axon growth, to provide protection from ischemia, glutamate toxicity, trauma and stroke, and to facilitate the action of various neurotropic factors and adhesion molecules. Although the mechanism by which GM1 exerts its effects is uncertain, one possibility is that GM1 binds to membrane protein receptors which, in turn, leads to second messenger activation.

The GM1 anti-idiotypic antibodies of the invention mimic GM1 in that they bind to and activate GM1 receptors and, through activation of a tyrosine kinase second messenger system, facilitate neuronal survival, adhesion and neurite growth.

The anti-idiotypic antibodies of the invention, including GM1 anti-idiotypic antibodies, can be produced using the method of Matthew and Sandrock (J. Immunol. Methods 100:73 (1987)). When a host is immunized with an antigen, advantageously, a simple antigen, and treated with cyclophosphamide as described by Matthew and Sandrock, the normal immune response is altered because those lymphocytes (B and T cells) that have been stimulated to divide are killed. It is the killing of T suppressor cells that, presumably, is responsible for the high frequency production of anti-idiotypic antibodies in animals treated with cyclophosphamide. That is, T suppressor cell killing results in the production of autoimmune responses, both to the antigen and to the newly elicited idiotypic antibodies. When spleen cells from such animals are immortalized, both idiotypic and anti-idiotypic antibodies are obtained. Antigens suitable for use in generating appropriate idiotypes using this system are, preferably, relatively simple, containing a limited number of epitopes. If a complex antigen possessing many non-functional epitopes is used, only a small number of idiotypic antibodies are successful at eliciting anti-idiotypes capable of binding the functional site of the antigen-binding protein. Simple carbohydrate structures (ranging from 2 to 6 saccharides) are preferred since the idiotypic response is essentially monoclonal in nature and most anti-idiotypic antibodies mimic the carbohydrate structure.

As noted above, GM1 has been shown to have very broad effects on neuronal growth and a variety of signaling mechanisms have been proposed to explain these effects. GM1 regulation of calcium homeostasis, either by influencing calcium channels, pumps or internal stores, is one possible explanation for the breadth of these effects. Accordingly, the present invention contemplates the use of anti-idiotypic antibodies of the type described herein to regulate calcium homeostasis which is fundamental to a variety of treatment regimens. Traumatic or ischemic brain injury is surrounded by an area, referred to as the area penumbra, of striking metabolic change. There are many changes that occur within the area penumbra, including an elevation in glutamate, glycine, GABA, amines, free radicals, and the products of arachidonic acid metabolism (Manev et al, FASEB J. 4:1789 (1990)). It is expected that those cellular responses to injury that can be regulated by GM1 can also be regulated by the GM1 anti-idiotypic antibodies of the invention.

In addition to the above, it is also expected that the GM1 agonist antibodies of the invention can be used to control the effects of glutamate toxicity in neurons. Glutamate depolarizes many types of neurons, opening voltage dependent and transmitter gated calcium channels, which increases intraneuronal calcium levels. In addition, glutamate can further increase calcium levels by activating receptors coupled to phosphatidylinositol. Such receptors increase inositol triphosphate which regulates internal calcium stores. By activating glutamate receptors and increasing post-synaptic calcium, the formation of arachidonic acid and and nitric oxide is activated (Manev et al., Acta Neurobiol. Exper. 50:475 (1990); Kiedrowski et al., J. Neurochom. 58:335 (1992)). Thus, some of the toxic effects of glutamate can be interpreted as being caused by persistent elevation of intraneuronal calcium levels leading to neuronal cell death. The ability of GM1 to provide protection against glutamate toxicity has been tested in vitro (Manev et al., Acta Neurobiol. Exper. 50:475 (1990); Nakamura et al., Methods Enzymol. 179:241 (1992); Manev, In: Bridging Basic anc Clinical Neuroscience, Georgetown Univ. Press (1993); Skaper et al., Dev. Brain Res. 71:1 (1993)) and in vivo (Lipartiti et al., Neuroreport 3:919 (1992)). In both sets of experiments, GM1 provides protection from toxicity. That GM1 regulation of calcium homeostasis is the basis for its broad effects on neuron growth is supported by experiments showing that GM1 affects calcium levels in neurons (Guerold et al., J. Neurosci. Res. 32:110 (1992); Hilbush and Levine, J. Biol. Chem. 267:24789 (1992)) and that GM1 modulates neurite outgrowth by regulating calcium (Spoerri et al., Dev. Brain Res. 56:177 (1990)). Precedent for GM1 regulation of calcium levels has been seen outside the nervous system where gangliosides inhibit platelet-derived growth factor-stimulated increases in intracellular calcium in fibroblasts (Guan et al., Biochim. Biophys. Acta 1136:315 (1991); Yates et al., Exp. Cell Res. 204:38 (1993)). The ability of GM1 agonist antibodies to regulate calcium homeostasis and provide protection against glutamate toxicity, makes possible many clinical uses for such antibodies, both within and beyond the nervous system.

Elevated levels of intracellular calcium can be toxic to neural as well as non-neural cells. Such toxicity can sometimes be controlled using calcium antagonists. Most notably, calcium antagonists can be used to inhibit the calcium toxicity in arterial hypertension and arteriosclerosis (Hansson, Acta Anaesthesiologica Scandinavica-Supplementum, 99:26–8, (1993)); Fleckenstein-Grun et al, Drugs, 44 Suppl 1:23–30, (1992)). Calcium antagonists significantly lower systolic and diastolic blood pressure (Fetkovska et al, American Journal of Hypertension, 6(3 Pt 2):98S-101S, (1993)). The effectiveness of anti-idiotypic antibodies to GM1 in regulating intracellular calcium levels, can be expected to make possible the treatment of a variety of diseases currently treated with calcium antagonists.

There is now extensive evidence for the early appearance and pathological importance of oxygen radical formation and cell membrane lipid peroxidation in the injured nervous system (Hall et al, Cell. Molec. Neuro. 13:415–432 (1993)). Furthermore, peroxide accumulation may lead to protein oxidation during aging (Stadtman, Science 257:1220 (1992)) which may be particularly toxic to individuals predisposed to neurodegenerative diseases. In addition, the neurodegenerative disorder, familial amyotrophic lateral sclerosis (ALS), has been shown to be associated with a mutation in superoxide dismutase (SOD), an enzyme responsible for eliminating free radicals in tissues (Marx, Science 261:956 (1993), Deng et al, Science 261:1047 (1993), Coyle et al, Science 262:689 (1993)). The GM1-agonist antibodies of the present invention afford protection against hydrogen peroxide toxicity and in a dose-dependent manner. (GM1, acting through GM1-binding proteins, can thus be expected to alter peroxide metabolism and protect neurons from oxygen free radicals (Dalia et al, J. Neurosci. 13:3104 (1993); Lai et al, Biochem. Pharm. 45:927 (1993)).) The agonist antibodies of the invention (eg the GM1-agonist antibodies) thus provide therapeutics for the treatment of tissue trauma, such as occurs in reperfusion injury, and for the treatment of oxidative-stress related diseases, including ALS, cancer, autoimmune diseases and AIDS (see Buttke et al, Immunol. Today 15:7 (1994)). The antibodies of the present invention are particularly advantageous for use in eliminating free radicals when long term treatments are required since such antibodies have long in vivo half lives. In the case of local tissue trauma or surgical procedure, agonist antibodies can be applied locally. For other purposes, the antibodies can be delivered intravenously.

The present invention also results from the observation that monoclonal antibodies can be produced that bind to Schwann cell surface molecules and, in so doing, stimulate tyrosine phosphorylation of specific protein substrates and dramatically facilitate cell migration. Schwann cells migrate extensively during development and regeneration of peripheral nerves. Thus, it is expected that antibodies against the Schwann cell membrane antigens can be used to enhance the therapeutic usefulness of Schwann cells following peripheral and central nervous system injuries where migration of Schwann cells promotes recovery.

Antibodies that potentiate Schwann cell migration can be produced using the immunosuppressant drug cyclophosphamide to tolerize the host to fibroblast membranes so that Schwann cell specific surface antigens can then be targeted (see Matthew and Sandrock, J. Immunol. Methods 100:73 (1987)). Schwann cells appear to follow certain molecular signals that govern their migration, thus they can be expected to possess specific surface receptors. Besides targeting the immune response in a subtractive scheme, cyclophosphamide can elicit autoimmune reactions (discussed above) and therefore success can be gained by the drug's ability to eliminate suppressive mechanisms. Mouse antibodies to a mouse Schwann cell line used in immunization are obtained even though it is extremely difficult to generate antibodies to mouse cell lines because the mouse is tolerant to these surface antigens. Therefore, a host treated with cyclophosphamide is susceptible to developing autoimmune reactions to normally non-immunogenic epitopes.

Schwann cell migration on biologically relevant tissue sections, and the effect of putative migration-modulating molecules (e.g. antibodies) thereon, can be studied using an in vitro bioassay. Briefly, dorsal root ganglia (DRG) from neonatal rats are explanted onto cryostat sections of either a normal sciatic nerve or a distal stump of previously transected sciatic nerve. Culture media suitable for use in the assay (for example, consisting of medium with fetal calf serum but without nerve growth factor) do not support significant neurite growth, but avidly support Schwann cell migration. The ganglionic Schwann cells that migrate on this substrate are visualized, for example, with the vital dye carboxyfluorescein di-acetate succinimydyl ester. The maximum distance migrated can be measured using an image analyzing program.

Numerous Schwann cells migrate extensively over sciatic nerve tissue substrates, mostly starting from 40 hours in culture. Assays are typically kept in culture for 72 hours in order to allow significant levels of Schwann cell migration to occur. Immunolabeling with a Schwann cell specific marker, S100, and counter staining with a nuclear marker, bis-benzamide, can be used to show whether all of the cells that migrate out of the DRG are Schwann cells. Typically, only occasional fibroblasts are seen among migrating Schwann cells. In some cases, a few neurofilament positive neurites are observed in the immediate region of the explant, far behind the migrating Schwann cells. Interestingly, Schwann cells migrate farther on a denervated sciatic nerve substrate than on a normal sciatic nerve substrate (for example, by 41%).

Various sources of Schwann cells have been tested in this assay system. Schwann cells from one day old superior cervical ganglia, sympathetic chain ganglia, coeliac ganglia (parasympathetic), neonatal sciatic nerve explants, and adult DRGs behave similarly in the assay. It is noteworthy that Schwann cells from sciatic nerve explants behave the same as Schwann cells from DRGs. The sciatic nerve explants do not contain neurons and therefore the bioassays provide a good model of Schwann cell behavior independent of neuronal influences.

One day old DRGs are used as the primary source of Schwann cells in the Examples that follow. They are easily obtained in large numbers and provide consistent results. Neonatal sciatic nerve explants are also used to verify results obtained with DRGs. As detailed in the Examples, following removal from one day old animals, sciatic nerves are cut into pieces and cultured for 48 hours in RPMI/10% FCS. Approximately 70% of the cells that migrate out during this period are fibroblasts. At the end of 48 hours, nerve pieces are explanted onto experimental nerve substrates and >95% of the cells that migrate out are Schwann cells (based on S100 staining). The advantage of such explants is that they lack neurons and contain mostly Schwann cells. However, unlike DRGs, it can be difficult to consistently obtain sciatic nerve explants that contain approximately equal numbers of Schwann cells. Therefore, it is advantageous to use DRGs for routine assays and to use sciatic nerve explants for verification.

The bioassay system described herein above provides an excellent strategy for screening antibodies (and other molecules) for their ability to influence Schwann cell migration and has the following advantages: 1) Schwann cells display their capacity to migrate differentially in response to different molecular environments, 2) this bioassay utilizes biologically relevant substrata and 3) it is simple enough that a large number of antibodies (or growth factors) can be easily tested for effects, 4) the predominant biological feature of this assay is Schwann cell migration, not fibroblast migration or neurite extension.

The in vitro bioassay described above mimics Schwann cell migration on extracellular matrix and basement membrane components. However, Schwann cells also migrate on axons during the development and regeneration of peripheral nerves. Described below are two different assays in which Schwann cells are sensitive to the activities of the molecules present on axonal surfaces.

In the first assay, neonatal DRGs are cultured on cryostat sections of adult trout olfactory nerve. Trout olfactory nerve is primarily made up of bundles of naked axons (Kreutzberg and Gross, Cell Tissue Res. 181:443 (1977)). An extremely high density of axonal packing is observed in this nerve and, in general, the ratio of axonal plasma membrane to glial plasma membrane in this nerve exceeds 7:1. Thus, Schwann cells migrating out of the DRG explant have the opportunity to migrate on axonal surfaces in this assay. Typically, greater than 95% of the cells that migrate out of the DRG are Schwann cells. The average distance of Schwann cell migration after 72 hours in culture is 428±13 µm. Other sources of pure axonal surfaces have been tested, such as, monolayers of a sensory neuronal cell line (E3H5B1), PC12 cells, and postnatal day 0 corpus callosum. Trout olfactory nerve is the preferred substrata for the purposes of this assay. This assay does, however, have certain limitations. Apart from the species origin of this substrate, the majority of the axons in a trout olfactory nerve do not seem to interact with glial cells during their development. These may, thus, contain certain molecular cues that signal fish glial cells to avoid them.

Schwann cell migration on axonal surfaces can also be studied using a second assay. In this assay, adult DRGs (L4, L5, L6) are removed two days after a sciatic nerve crush, dissociated, and cultured at low density on laminin coated plates in culture medium, for example, F1 5/10% horse serum. The dissociation procedure results in small neuron-Schwann cell clumps of similar size (~70 µm in diameter). Observation of cultures at, for example, 5, 16, 24, and 36 hours, indicates that by about 10 to 16 hours in culture, neurons in the clump establish extensive neurite networks. Following this, Schwann cells in the neuron-Schwann cell clump begin to migrate along these neurites. Schwann cells are easily identified based on their classical bipolar morphology. Almost all of the Schwann cells seen on neurites must originate from the neuron-Schwann cell clump, since only occasional Schwann cells are observed outside neuron-Schwann cell clumps during the early time points in culture. Time-lapse recordings of these cultures show that Schwann cells migrate exclusively along neurites and these cells always originate from the aggregate. Migration is not unidirectional but Schwann cells can change direction and migrate back towards the aggregate.

The major advantage of this assay is that it provides an optimal system to monitor the migration of Schwann cells on living neurites in real time. Moreover, some of the secondary events associated with changes in the migratory state of Schwann cells (e.g., filopodia extension or collapse) and changes in neurite growth and morphology can also be characterized in this assay. The ability of various agonist antibodies (and other molecules) to modulate these biological phenomena can be easily tested in this assay by including them in the culture media. One skilled in the art will appreciate that these assays can be used in combination to screen for antibodies (and other molecules) that modulate axon-Schwann cell interactions.

Although the Examples set forth below relate specifically to antibodies that bind Schwann cell surface molecules and facilitate cell migration and to antibodies to GM1 binding proteins that promote neuronal growth, the invention has much broader applicability. For example, antibodies can be produced in accordance with the invention that facilitate wound repair. For tissue and skin to recover from either wounds or burns, specific cell types must migrate to replace the damaged tissues. The availability of agonist antibodies that facilitate the migration of skin cells is clearly of advantage for use in treating tissue damage. Antibodies that facilitate Schwann cell migration can be expected to be suitable for use in promoting skin cell migration. Alternatively, antibodies that promote skin cell migration can be produced by targeting skin cell specific antigens in the manner described above for Schwann cell surface antigens.

The invention also contemplates agonist antibodies that stimulate the function of specific immune cells compromised by, for example, HIV infection. In this regard, it is expected that immune cell function can be promoted by using agonist antibodies that mimic lymphokines. The anti-idiotypic strategy can be employed to develop agonist antibodies by identifying the functional site of the lymphokine. Alternatively, antibodies can be generated to the lymphokine receptor that are capable of mimicking the lymphokine.

Agonist antibodies of the invention also include those that mimic the function of growth factors. That is, agonist antibodies can be used that bind and activate growth factor receptors. For example, an agonist antibody for the insulin receptor can be used in place of insulin. Neurotrophic factors can be mimicked with antibodies and thereby provide therapies for motor neuron disease and Alzheimer's disease. Furthermore, it is expected that essentially any pharmaceutical that acts at the cell surface can be mimicked with an agonist antibody of the invention. Such pharmaceuticals include manufactured drugs as well as endogenous agents that promote cellular functions. In each case, the antibody is targeted to the functional active site of the receptor. Difficulties in applying this approach, in terms of targeting the antibody to the appropriate site on the receptor protein, can be expected to be resolved by using the anti-idiotypic method to target the functional recognition site on the receptor. The use of anti-idiotypic antibodies directed to the functional domains of proteins are ideal for this purpose, since such antibodies mimic the structure of the ligand, not the structure of the binding protein.

While the present approach is applicable to any ligand (small ligands being preferred), carbohydrate-binding proteins are particularly preferred targets for therapeutic agonist antibodies. Carbohydrate drug development is being sought for a wide variety of diseases: AIDs, arthritis, cardiovascular disease, diarrhea, infections, anti-inflammatory, autoimmune disease, diabetes, and wound healing (The Genesis Report, Vol. 1, number 2 (1992)). The intent in these efforts is to develop specific carbohydrates that interact with carbohydrate-binding proteins. The major dilemma continues to be the production of pure carbohydrates in large quantities. This dilemma can be resolved by developing anti-idiotypic antibodies to the carbohydrate of interest and using the antibody to mimic the carbohydrate structure in the manner described above for GM1 and the GM1 receptor.

Agonist antibodies of the invention that are preferred for use in humans can be designed using approaches such as those that follow. Chimeric antibodies can be made where variable regions from mouse agonist antibodies are spliced to human constant regions. Alternatively, those regions of mouse agonist antibodies comprising the binding site can be grafted into human antibodies. The latter is typically referred to as a "humanized" antibody. In both cases, because the constant region of the immunoglobulin is responsible for eliciting an immune response, the antibodies are relatively non-immunogenic in humans. Either chimeras or humanized murine antibodies can be produced by cloning the cDNA for the antibody and genetically engineering the recombinant immunoglobulin molecules (Mountain and Adair, Biotech. Genetic Engin. Rev. 10:1–142 (1992); Singer et al, J. Immun. 150:2844–57 (1993); Hardman et al, Inter. J. Biol. Markers 7:203–9 (1992); Carter et al, P.N.A.S. 89:4285–9 (1992)). Another, more simple approach, is to use Fab fragments of mouse antibodies (Hudson and Hay, Practical Immunology, Blackwell Sci. Pub. (1989)). In this case, the majority of the constant region is removed by proteolysis. This yields a protein with the ability to bind antigen but one that is incapable of activating complement. This approach is preferred since agonist antibodies of the invention are used to signal cells through receptors, not to activate complement and kill cells.

The agonist antibodies of the invention are preferable to most pharmaceuticals and peptides in that they are long-lived in the body. Immunoglobulins turn over in vivo with half lives of approximately 30 days. By comparison, the half life of GM1 in vivo ranges from 6 to 24 hours. In addition to a prolonged half life, antibodies of the invention that have a high affinity for their respective binding partners can be more effective than the molecules they mimic.

The mode of delivery of an antibody of the invention depends on the nature of the antibody and the therapeutic effect to be achieved. For applications relating to peripheral nerve regeneration, the delivery of antibody is relatively straightforward. Delivery of antibodies of the invention to the brain can, however, also be effected and without compromising the blood brain barrier. The barrier is not absolute, but typically reduces the concentration of serum proteins by three orders of magnitude. A high affinity, potent agonist antibody might have an effect within the brain at such titers. In cases of tissue trauma, either within the nervous system or peripheral injuries, like wounds, an agonist antibody of the invention that promotes cell survival, growth or migration can be applied locally, for example, by the surgeon during surgery to reconstruct the cord or eliminate hemorrhaging. Agonist antibodies that promote neuron growth can be directly applied to the site of surgery. In addition, canuli left in place to drain the lesion can be used to deliver therapeutic agents. Antibodies can also be delivered into the cerebral spinal fluid using standard techniques.

In the case of burns or wounds, agonist antibodies can again be applied locally. For other purposes, the antibodies can be delivered intravenously. Doses of agonist antibodies that are effective but that do not cause secondary complications can be experimentally determined.

Since agonist antibodies are designed to facilitate the survival, growth and migration of certain cell types, they will be valuable tools for supplementing currently available therapeutics. For example, it is expected that agonist antibodies can be developed that potentiate the activity of certain growth factors and that these two reagents can be employed in combination.

Certain aspects of the present invention are described in greater detail in the non-limiting Examples that follow.

EXAMPLE I

Promotion of Neuron Growth by Antibodies to GM-1 Binding Proteins

I.a. Generation of Antibodies to GM1-binding Proteins:

GM1 (3.5 mg) was solubilized in 0.5 ml of absolute ethanol and added to 0.7 mg of glutaraldehyde-activated beads (Affinity Adsorbent, 665–525, Boehringer Mannheim). The ethanol was evaporated under a stream of nitrogen gas and the beads were suspended in 7.0 ml RPMI-1640 culture medium. Female BALB/c mice, 8 weeks old, received a 1 ml volume of bead suspension i.p. containing 0.5 mg of ganglioside. Cyclophosphamide (2 mg/ml in saline) was given i.p. at dosages of 100 mg/kg and/or 150 mg/kg. A final dose of 0.5 mg of GM1 was given two weeks after the initial immunization. Spleens were removed 2–4 days later for fusion. Spleen cells of immunized mice were fused with NS1 myeloma cells as described (Matthew and Sandrock, J. Immunol. Methods 100:73 (1987); Dunbar and Skinner, Methods Enzymol. 182:670 (1990)).

The antibodies were screened in ELISA's (Ausubel et al, Current Portocols in Molecular Biology, Vols. 1 and 2, John Wiley & Sons (1990); Matthew and Sandrock, J. Immunol. Methods 100:73 (1987); Miyoshi et al, J. Biochem. 92:89 (1982)) for their ability to bind to purified GM1, GM2, GD1b, a mixture of gangliosides that includes GM1, galactocerebroside (the ganglioside backbone with only a galactose sugar moiety rather than the full complement of carbohydrates), and the $\beta$ subunit of cholera toxin. Gangliosides and galactocerebroside were solubilized in methanol at a concentration of 10 $\mu$g/ml. Fifty $\mu$l was pipetted into each well of a 96 well ELISA plate and the solvent evaporated in a fume hood. Cholera toxin (beta-subunit) was diluted to 5 $\mu$g/ml; 50 $\mu$l was pipetted into each well of a 96 well ELISA plate and allowed to adsorb to the plastic for 2 hours at room temperature or overnight at 4° C. The plates were washed with 1% PVP/TBS and 50 $\mu$l of hybridoma supernatant or NS1 conditioned media was added to each well. After a one hour incubation, the wells were washed and incubated with biotinylated anti-mouse IgG and IgM's. The biotinylated secondary antibodies were incubated with avidin-HRP (Vectastain ABC kit, Vector Labs). The complex was visualized as a diaminobenzidine reaction product (Ausubel et al, Current Protocols in Molecular Biology, Vols. 1 and 2, John Wiley & Sons (1990)).

Using seven different immunization schedules, 1467 hybridomas were produced. Twenty hybridomas were selected from each fusion to be screened for antibody specificity. Of these 140 hybridomas, 44 produced antibody secreting hybridomas. Of the 44, 16 were identified as putative anti-idiotypic antibodies based on their ability to bind cholera toxin. Two doses of cyclophosphamide produced the greatest number of hybridomas secreting ganglioside or cholera toxin binding antibodies. In this series of fusions, 36.4% of the antibody-secreting hybridomas produced antibodies specific for the beta-subunit of cholera toxin. This binding was blocked competitively by GM1.

I.b. Spatial and Temporal Distribution of Antigens:

ELISA assays: Homogenates of brain tissue from rats aged embryonic day 18, postnatal days 0 and 7 and adult were prepared in TBS. The protein contained in each of the 4 homogenates was determined with a Biorad protein assay and the homogenates were each diluted to a final protein concentration of 32 mg/ml. Fifty $\mu$l of homogenate was added to each ELISA well and allowed to adsorb for 2 hours at room temperature or overnight at 4° C. The ELISA assay was performed as described by Matthew and Sandrock (J. Immunol. Methods 100:73 (1987)) and Miyoshi et al (J. Biochem. 92:89 (1982)).

Labeling tissue sections: Neonatal rats (aged 0–10 days) were anesthetized in the cold and adult rats were anesthetized with a combination of ketamine (100 mg/kg), xylazine (5.2 mg/kg) and acepromozine (1 mg/kg) and perfused in 2–4% paraformaldehyde in phosphate buffered saline with 2% sucrose. Tissue was removed and frozen to a cryostat chuck with OCT embedding media. Fifteen micrometer sections were cut at −18° C. onto subbed glass slides. Sections were washed and blocked in 1% PVP/TBS or 2.5% calf serum/TBS and primary and fluorescently labeled secondary antibodies applied for 1 hour each at room temperature.

Culture methods for dissociated hippocampal cells: Hippocampi were dissected from embryonic day 18 rats. The meninges are removed and the cells are incubated at 37° C. in Ca++, Mg++ free Hank's buffered salt solution (fHBSS) with 0.005% (w/v) trypsin for 15 minutes. The cells are washed in DMEM/F12 media with 5% horse serum and 2.5% calf serum and triturated. The cells were spun and resuspended to a final concentration of 50–200K cells/ml (adapted from Banker and Cowan, Brain Res. 126:397 (1977); Banker and Goslin, Culturing Nerve Cells, MIT Press, Cambridge, Mass., pp. 177–206 and 251–282 (1991)).

Labeling cells in culture: Dissociated cells were plated onto glass chamber slides coated with poly-L-lysine, laminin, or on a monolayer of astrocytes. The cells were allowed to grow until neurites formed (3–5 days). Cultures were fixed with 4% paraformaldehye and permeabilized with 0.3% TRITON (a non-ionic detergent)-X-100. Coverslips were rinsed with medium, incubated with hybridoma supernatant for 30 minutes, washed with 1 PVP/TBS or 2.5% calf serum in tris buffered saline pH 7.4 (CS/TBS), incubated with fluorescein coupled goat anti-mouse Ig (Antibodies Inc.) for 30 minutes, washed with CS/TBS and then viewed using a fluorescence microscope. Neurons were identified with an anti-neurofilament monoclonal antibody, astrocytes were identified with anti-glial fibrillary acidic protein, oligodendrocytes were identified using anti-galactocerebroside monoclonal antibody and fibroblasts were identified by labeling with antibodies to fibronectin.

The 16 antibodies referenced in I.a. above that bound the beta subunit of cholera toxin were screened for their ability to bind to.brain homogenates in ELISA assays, cultured embryonic hippocampal cells and sections of CNS and PNS tissue. All of these antibodies bound to tissue homogenates from developing brains in the ELISA's. These antibodies were then used to label tissue sections and cultured cells, as described above. Ten of these antibodies labeled tissue sections and 5 labeled cultured cells.

I.c. In Vitro Axon Outgrowth Bioassay on Cryostat Sections:

Bioassays: Dissociated cells were plated at 20–35 k cells/cm$^2$ onto substrates of increasing complexity: poly-L-lysine (Banker and Cowan, Brain Res. 126:397 (1977)), CELL-TAK cryostat sections of E18 brain and spinal cord (Tuttle and Matthew, J. Neuro Sci. Methods 39:193 (1991)), adult normal sciatic nerve and the distal stump of a degenerating sciatic nerve (Sandrock and Matthew, Proc. Natl. Acad. Sci. USA 84:6934 (1987)) in the presence of hybridoma supernatant or NS1 conditioned media. Living cells were visualized with fluorescence microscopy following incorporation of the vital dye 6-carboxyfluorescein diacetate succinimidyl ester (Bronner-Fraser, J. Cell Biol. 101:610 (1985)); Rotman and Papermaster, Proc. Natl. Acad. Sci. USA 55:134 (1966)).

Measuring the degree of neurite outgrowth: The total length of neurite outgrowth was measured from cells whose processes were at least as long as the diameter of the cell body. All the processes measured in this study were single unbranched neurites. When the processes were bipolar, the length of both processes were added to give a total neuritic length.

Four of 10 antibodies from I.a. above that were tested (designated 4, 5, 20 and 58) were successful in manipulating cell attachment and neurite outgrowth in in vitro bioassays (see FIGS. 2A, 2B, 3A–3C and 4). All of these antibodies promoted cell adhesion and promoted process outgrowth to brain sections. In only 5% of the control bioassays, did cells attach to brain sections. Only 1 antibody was successful in promoting attachment to embryonic spinal cord. All of these antibodies promoted cell adhesion to the normal sciatic nerve. In 7 of these bioassays, attached cells exhibited processes. In control bioassays, cells never attached to the normal sciatic nerve. Cells always adhered to the distal stump of a degenerating sciatic nerve in control and antibody treated bioassays.

Antibodies that bind to cholera toxin thus have the ability to promote cell adhesion and neurite outgrowth on nonpermissive substrates. Embryonic hippocampal cells were plated onto: a) E18 brain, b) E18 spinal cord, c) adult normal sciatic nerve, and d) distal stump of a transected sciatic nerve. Cells adhere to permissive and nonpermissive substrates when they are cultured in the presence of the anti-idiotypic antibodies.

Further studies demonstrated that the anti-idiotypic antibodies actually enhanced the ability of the cells to adhere to and survive on permissive and nonpermissive substrates rather than merely covering inhibitory sites on the substrates. Specifically, the cells were grown on simple substrates like poly-L-lysine or CELL-TAK in the presence of antibody or NS1 conditioned media. In these assays, cells adhere readily to CELL-TAK and extend processes. After 3 days in culture, cells grown in the presence of antibody had extended single or bipolar unbranched neurites the total neuritic length of which was 50–75% longer than those grown in the presence of NS1 conditioned media (see FIG. 4).

I.d. Determination of Proteins that are Phosphorylated at Tyrosine Residues in Response to Antibody Treatment:

Dissociated embryonic hippocampal cells were prepared. Five hundred μl of cells at 200K cells/ml were incubated for 45 minutes in the presence of 500 μl of various hybridoma supernatants, 0.5 or 0.1 μg of cholera toxin, 2 or 20 μg of GM1, the phosphatase inhibitor vanadate (0.5 mM) or kinase inhibitor genestein (0.5 mM), and NS1 conditioned media. These growth factors represent two major classes of growth factors that act in the nervous system (Cockram et al, Sem. in Dev. Biol. 1:421–435 (1990); Maisonpierre et al, Sci. 247:1446–1451 (1990); Unsicker et al, PNAS 84:5459–5463 (1987); Walicke et al, PNAS 83:3012–3016 (1986)). The cells were pelleted and the supernatant aspirated with a 27 gauge needle. Hot SDS-PAGE sample buffer containing 0.5 mM vanadate was added and the samples were frozen at −20° C. until use. The samples were boiled and centrifuged; 30 μl was added to each well of a 10% gel and run at 40 mA. The proteins were blotted onto nitrocellulose, blocked with 4% calf serum containing vanadate and then 10% calf serum in tris buffered saline (pH 7.4) overnight at 4° C. Bands of protein containing phosphorylated tyrosine were identified using an anti-phosphotyrosine antibody (Sigma, P-3300) diluted 1:750 in 10% calf serum. Positive bands were visualized with an anti-mouse VECTASTAIN ABC-HRP kit as a diaminobenzidine reaction product.

As shown by Western blotting, embryonic hippocampal cells treated with anti-idiotypic antibodies that promote cell adhesion and neurite outgrowth induced tyrosine phosphorylation of bands at approximately 65–75 and 48–52 Kd. The bands of tyrosine phosphorylation were not observed in samples treated with nonfunctional antibodies, NS1 conditioned media, 0.5 mM genestein, 0.5 mM vanadate. Proteins that are known to be phosphorylated in neurons are as follows. For the 75 kD band: 80 kD synapsin 1 (synaptic vesicle protein), 72 kD protein phosphorylated at serine in response to GQ1b (Nakamura et al, J.N.R. 31:724 (1992)), 70 kD paxillin (a protein in focal adhesions, substrate for the tyrosine kinase pp60src), the 69 kD laminin receptor, 68 kD neurofilament protein, or 59 kD vimentin. For the 50 kD band: 45 kD NGF activated MAP2 kinase, 42–44 MAP kinase (ERK), 46 kD talin, 45 kD laminin binding protein, 43 kD actin, 36–42 kD proteins of rat brain P2 subcellular fraction, P in response to GD1b (Bassi et al, J. Neurochem. 57:1207–1211 (1991).

I.e. Molecular Identity of Antigens Recognized by the Anti-idiotypic Antibodies:

Embryonic hippocampal cells or PC12 cells were solubilized with SDS and mercaptoethanol. The material was separated by SDS-PAGE and electrophoretically transferred to nitrocellulose paper. The blot was blocked with 1% PVP/TBS, incubated with hybridoma supernatant, washed with CS/TBS and incubated with biotinylated anti-mouse IgM. The bound antibody was detected using a VECTASTAIN AIBC-HRP kit and the complex was visualized as a diaminobenzidine reaction product (Ausubel et al, Current Protocols in Molecular Biology, Vols. 1 and 2, John Wiley & Sons, N.Y. (1990)).

Western blotting of the embryonic hippocampal and PC12 cells revealed bands at approximately 45 and 57 kD that are recognized by the anti-idiotypic antibodies that enhanced adhesion and neurite outgrowth in bioassays. These bands were recognized regardless of whether the cells had been cultured in the presence of growth factors. The antibodies tested appeared to show differential affinity for cholera toxin, beta-subunit, in the ELISA assays, and also showed varied affinities for the proteins on the blot. In all cases, the 45 kD band was recognized more strongly than the 57 kD band.

In order to determine whether the antibodies were binding to the carbohydrate portion of the protein, three experiments were performed. Western blots showed that antibody binding was not blocked by preincubating the antibodies with the appropriate carbohydrates, that samples treated with glycosidases continue to be labeled with the antibodies, and the antigen could be recognized by antibodies in PC12 cells grown in the presence of tunicamycin which inhibits protein glycosylation. In each case, recognition of the 45 and 57 kD bands on the Western blot indicated that the antibodies did not bind to the carbohydrate portion of a protein.

EXAMPLE II

Modulation of Schwann Cell Migration by Antibodies Against Schwann Cell Membrane Antigens I In Vitro Bioassays I.a) In Vitro Bioassay for Schwann Cell Migration on Cryostat Tissue Sections:

In this assay, neonatal peripheral ganglia are cultured on cryostat sections of sciatic nerve and migration of Schwann cells from the peripheral ganglia onto the nerve substrate is assessed. The assay provides an in vitro system where the primary biological event is Schwann cell migration on extracellular matrix and cell surfaces, not neurite extension or fibroblast migration. Neurite outgrowth is minimal when a simple culture medium is used (RPMI/10% FCS or DMEM/10% FCS, lacking exogenous additives like NGF). The extent of Schwann cell migration, neurite outgrowth, and fibroblast migration has been evaluated by first immunostaining the cultures with Schwann cell and neuron specific markers such as S100 and GAP-43 and then counterstaining them with cresyl violet or bis-benzamide.

Method: Twenty two micron thick longitudinal cryostat sections of adult sciatic and optic nerves are dried on to glass coverslips and then washed briefly in DMEM. DRGs from one day old rats are removed, treated with 0.25% trypsin and 200 units/ml collagenase in DMEM for 20 minutes, rinsed with 0.1% anti-trypsin and 0.01% DNAse in DMEM/10% FCS for 10 minutes, and then explanted onto the cryostat sections. Cultures are maintained in DMEM/10% FCS from one to three days. At the end of incubation, a vital dye, 5–6 carboxyfluorescein diacetate succinimydyl ester, is used to visualize cells and neurites. Images of these living cultures are recorded. Following the vital dye treatment and image acquisition, cultures are fixed in 4% parafornmaldehye and stained with antibodies to S100 and neurofilament either the peroxidase-anti-peroxidase method or the immunofluorescence method (Hudson and Hay, Practical Immunology, Blackwell Sci. Pub. 1989). Depending on the histochemical procedure used, cultures are counterstained with either cresyl violet or bis benzamide. In addition to DRGs, parasympathetic ganglia, sympathetic chain ganglia and sensory ganglia from different points along the rostrocaudal axis (at least one antigen differs along the rostrocaudal axis among Schwann cells—see: Suzue et al, Neuron 5:421 (1990)) have been tested in this assay as possible sources of Schwann cells and to ascertain any differences in their capacity to migrate. Sciatic nerves from different age rats (embryonic day 14 to adult) have been cut into 2 mm segments and explanted onto tissue sections.

The IMAGE I (Universal Imaging Inc.) program is used to measure the extent of Schwann cell migration in this assay. A rectangular grid divided into several 100 square micrometer squares is pasted to the image and the distance between the edges of the DRG and the leading Schwann cells is measured. An average of these measurements indicates the mean distance Schwann cells have migrated on a particular substrate from a particular DRG explant. These measurements are analyzed using a statistics software program, EXSTATICS.

I.b.) In Vitro Bioassay to Study Schwann Cell Migration on Axonal Surfaces:

In the assays that follow, Schwann cells are sensitive to the activities of molecules present on axonal surfaces. In the first assay, cryostat sections of a nerve (trout olfactory nerve) that is primarily made up of naked axons are used as substrates for Schwann cell migration. In the second assay, living axons are used as substrates. In both cases, migrating Schwann cells interact primarily with axonal surfaces.

Culture methods for dissociated dorsal root ganglion (DRG) cells: Neonatal rats were anesthetized in the cold and decapitated. DRG were removed and incubated at 37° C. in 0.25% collaganase type 11 in F14 media with N1 additives for 1.5 hours. DRG were then triturated and 0.025% (w/v) trypsin 80 g/ml DNAase and 100 g/ml soybean trypsin inhibitor is added. Following one round of gentle trituration, the cells are suspended in 15 ml of F14 media with 10% horse serum and spun. The pellet is resuspended to 50–200K cells/ml and incubated or plated on poly-L-lysine ((0.1 mg/ml) or laminin (10 mg/ml) coated glass coverslips.

Culture methods for dissociated superior cervical ganglion cells: Ganglia were dissected from 2–3 day old mice, and the capsule is removed. The ganglia were incubated at 37° C. in Ca++, Mg++ free Hank's buffered salt solution (fHBSS) with 0.25% (w/v) trypsin for 30 minutes. The cells are transferred to L-15 media with 1 mg/ml BSA, washed twice, and triturated. The cells are spun and resuspended to a final concentration of 50–200K cells/ml (adapted from Banker and Goslin, Culturing Nerve Cells, MIT Press, Cambridge, Mass., pp. 177–206 and 251–282 (1991)) and plated onto poly-L-lysine coated coverslips.

Assay: In the first assay, Schwann cell migration on 22 $\mu$m thick trout olfactory nerve substrates was studied in a manner analogous to that described above for Schwann cell migration on cryostat sections of sciatic nerve. For the study of Schwann cell migration on living neurites, sciatic nerves of adult Sprague-Dawley rats were crushed two days prior to the removal of corresponding DRGs (L4, L5, and L6). Following removal, DRGs were incubated at 37° C. in 0.25% collagenase type II (in F14 media with N1 additives) for 1.5 hours. At the end of this incubation, DRGs were triturated (16 passages) with a fire polished glass pipette and 0.025% trypsin was added to the cell suspension. After 15 minutes at room temperature, 80 $\mu$g/ml DNAse and 100 $\mu$g/ml soybean trypsin inhibitor were added to the suspension. Following one round of gentle trituration, cells were suspended in 15 ml of F14/10% horse serum (HS) media and spun for 10 minutes at 500 g. The cell pellet was resuspended in a desired volume of F14/10% HS and plated on laminin (10 $\mu$g/ml) coated 24 well plates. In general, the cells from one DRG were plated into 32 wells. Cultures were maintained for 36 hours and then stained with 5–6 carboxyfluorescein diacetate succinimidyl ester and bis benzamide. Carboxyfluorescein labels all living cells and their processes. Bis benzamide was used to stain the cell nuclei. Images of cultures stained as above could be used to analyze the extent of neurite outgrowth and neuron-Schwann cell association. Instead of labeling with carboxyfluorescein and bis-benzamide, migration of Schwann cells on neurites has also been monitored in real time in cultures using time lapse microscopy.

I.c.) Assay to Determine Whether Schwann Cells from Dystrophic Mice Differ in Their Ability to Migrate and Whether Dystophic Nerve Substrates Differ in Their Ability to Support Schwann Cell Migration:

In the spinal nerve roots of dystrophic mice, substantial numbers of axons are without ensheathment and are not separated by Schwann cell processes or extracellular matrix. In these regions, Schwann cells are present but they remain on the perimeter of the bundled axons. These observations imply a deficit in Schwann cell migration during development. Therefore, the migratory behavior of dystrophic Schwann cells and the molecular differences between normal and dystrophic nerve substrates can be analyzed as follows.

Method: Cryostat sections of sciatic nerves from dystrophic mice and littermates are used as substrates. DRGs from normal and dystrophic mice are explanted on to these substrates. Migration of normal Schwann cells on dystrophic nerve substrate, dystrophic Schwann cells on normal nerve substrate, and dystrophic Schwann cells on dystrophic nerve substrate are assessed as described above. Relevant growth factors and antibodies are tested in these assays for their ability to alleviate the deficits in Schwann cell migration.

Cryostat sections of sciatic nerves from dystrophic and normal mice are screened by immunocytochemistry with relevant antibodies.

II Preparation of Monoclonal Antibodies and Potentiation of Schwann Cell Migration II.a.) Antibodies Prepared to Schwann Cell Molecules:

The cyclophosphamide protocol of Matthew and Sandrock (J. Immunol. Methods 100:73 (1987)) was used to isolate monoclonal antibodies that recognize antigens expressed by Schwann cells. Briefly, mice were tolerized first with whole cell extracts from fibroblast cell line (3T3) and then immunized with whole cell extracts from the Schwann cell line B1.1, a cell line generated by infecting primary mouse Schwann cells with a transforming retrovirus. Cell lines were used since large quantities of pure, homogeneous populations could be generated efficiently.

About 90 antibodies were identified that recognize antigens expressed in B1.1 cells but not in 3T3 cells. These 90 antibodies also recognize Schwann cell associated antigens in cryostat tissue sections of sciatic nerve and primary Schwann cells. Immunostaining of sciatic nerve sections indicate that 60 of the antibodies recognize extracellular matrix or myelin associated antigens. Sixteen others recognize Schwann cell membrane associated antigens and fourteen antibodies bind Schwann cell cytoplasmic antigens. These antibodies are referred to as S series antibodies.

II.b. Potentiation of Schwann Cell Migration in Vitro by Monoclonal Antibodies:

All of the antibodies that were raised against B1.1 cell line were screened in the in vitro bioassay for Schwann cell migration on cryostat sections of normal and denervated sciatic nerve, as described above. The antibodies that modulated Schwann cell migration in this assay were further screened for their ability to modulate Schwann cell migration on trout olfactory nerve sections and living neurites using the assays set forth above. Time lapse recordings permit measurements of true neurite growth and Schwann cell migration rates in the assays to evaluate Schwann cell migration on living axons. In light of the large numbers of antibodies to be screened, only the changes in the number of Schwann cells associated with living neurites and the extent of neurites in the presence or absence of the antibodies were evaluated. Any modulation of axon-Schwann cell interactions by the antibodies is expected to be reflected in these two phenomena. Primary Schwann cells and fibroblasts were stained with these antibodies in order to identify the cellular location of the corresponding antigens. Furthermore, these antibodies were also isotyped and tested in dot blots for their ability to recognize extracellular matrix molecules, laminin, and fibronectin. Listed in Table 1 are antibodies that were found to potentiate Schwann cell migration and antibodies that were found to inhibit Schwann cell migration (note that antibody 21 (IgG1) was obtained from a fusion different from the fusion that resulted in the other antibodies listed).

TABLE 1

RESULTS OF BIOASSAYS & PRELIMINARY BINDING CHARACTERISTICS

| Antibody | Bioassay #: | | | | | Binding to: | | | | | | |
| --- | --- | --- | --- | --- | --- | --- | --- | --- | --- | --- | --- | --- |
| | #1 NS | #2 DS | #3 TN | #4 | #5 | SC | FB | EM | LN | FN | MYL | Ig clas |
| S131C | -- | -- | - | • | • | + | + | - | - | - | - | M + G2 |
| S122B | -- | -- | • | •/+ | • | + | + | + | + | - | - | M |
| S113G | • | -- | • | • | - | + | + | + | - | + | - | G1 |
| S159H | -- | -- | • | • | - | + | - | - | - | - | - | M |
| S216B | - | - | • | • | • | + | - | - | - | - | - | M |
| S139G | - | - | - | • | • | + | - | - | - | - | - | A |
| S224G | --- | --- | • | • | • | + | - | - | - | - | - | M |
| S135C | -- | -- | - | • | • | + | + | - | - | - | - | M + G1 |
| S1410H | --- | --- | - | • | • | + | - | - | - | - | - | M |
| S147C | • | - | • | • | • | + | - | - | - | - | - | G2a |
| S212A | - | - | - | •/+ | - | + | - | + | + | + | - | M |
| S143C | • | - | nd. | nd. | nd. | + | + | - | - | - | - | M + G1 |
| S138E | • | ++ | • | • | • | + | + | - | - | - | - | M + G2 |
| S241D | ++ | • | -/• | • | + | + | + | - | - | - | - | M + G1 |
| S1211G | + | • | • | • | • | + | - | + | - | - | +,+ | M |
| S222H | ++ | • | • | • | • | + | - | - | - | - | - | M + G1 |
| S112B | ++ | • | -/• | + | + | + | - | - | - | - | - | M |
| S122C | ++ | • | • | • | • | + | - | - | - | - | - | G1 + M |
| S113D | ++ | • | + | + | • | + | + | - | - | - | - | M |
| S126B | ++ | • | • | ++ | • | + | + | - | - | - | - | M + G1 |
| S1410G | ++ | • | • | ++ | • | + | - | - | - | - | - | M + G1 |
| S237E | + | • | • | • | • | + | - | - | - | - | +,+ | M |
| S119H | ++ | • | • | • | • | + | - | - | - | - | - | M |
| S131B | ++ | • | + | • | • | + | - | - | - | - | - | M + 2b |
| S126E | ++ | • | • | • | • | + | - | - | - | - | - | nd. |
| S137G | ++ | • | • | • | • | + | - | - | - | - | - | M + G1 |
| S119C | ++ | • | • | • | • | + | - | + | + | + | - | M + G1 |
| S135E | +++ | • | • | ++ | • | + | - | - | - | - | - | M |
| S2110B | + | • | +- | + | • | + | - | - | - | - | - | G1 |
| S216C | +++ | • | nd. | + | + | + | - | - | - | - | - | A |

TABLE 1-continued

RESULTS OF BIOASSAYS & PRELIMINARY BINDING CHARACTERISTICS

| | Bioassay #: | | | | | Binding to: | | | | | | |
|---|---|---|---|---|---|---|---|---|---|---|---|---|
| | #1 | #2 | #3 | | | | | | | | | |
| Antibody | NS | DS | TN | #4 | #5 | SC | FB | EM | LN | FN | MYL | Ig clas |
| 21* | +++ | • | nd. | nd. | nd. | + | – | – | – | – | – | G1 |
| 4,5,20,58** | +++ | • | nd. | nd. | nd. | + | nd. | nd. | nd. | nd. | nd. | all M's |

BIOASSAY #1: EVALUATION OF SCHWANN CELL MIGRATION ON CRYOSTAT SECTIONS OF NORMAL SCIATIC NERVE (NS).
BIOASSAY #2: EVALUATION OF SCHWANN CELL MIGRATION ON CRYOSTAT SECTIONS OF DENERVATED SCIATIC NERVE (DS).
BIOASSAY #3: EVALUATION OF SCHWANN CELL MIGRATION ON CRYOSTAT SECTIONS OF TROUT OLFACTORY NERVE (TN).
BIOASSAY #4: EVALUATION OF NUMBER OF SCHWANN CELLS ASSOCIATED WITH NEUTRITES FROM DISSOCIATED ADULT DRG CULTURES.
BIOASSAY #5: EVALUATION OF NEURITE GROWTH FROM ADULT DRG CULTURES (EXTENT OF NEURITE GROWTH AND BRANCHING).
ANTIBODY EFFECTS ON BIOASSAYS:
•: SAME AS CONTROL
– OR +: 25%–50% ENHANCEMENT(+) OR REDUCTION(–)
–– OR ++: 50%–75% ENHANCEMENT OR REDUCTION
––– OR +++: ABOVE 75% ENHANCEMENT OR REDUCTION
ND: NOT DETERMINED
BINDING: BINDING TO SCHWANN CELLS(SC) AND FIBROBLASTS(FB) REPORTS IMMUNOHISTOCHEMICAL RESULTS FROM STAINING PRIMARY CULTURES OF SCHWANN CELLS AND FIBROBLASTS. BINDING TO EHS SARCOMA MATRIGEL EXTRACELLULAR MATRIX(EM), EHS LAMININ(LN), HUMAN PLASMA FIBRONECTIN(FN), PREPARATIONS OF PERIPHERAL AND CENTRAL MYELIN(MYL) ASSAYED BY DOT BLOT AND ELISA ASSAYS. THE TOW ANTIBODIES THAT BIND MYELIN BIND BOTH CNS AND PNS MYELIN PREPARATIONS.
IMMUNOGLOBULIN(IG) CLASS DETERMINED USING A HYCLONE ISOTYPING KIT. ONLY SOME CELL LINES HAVE BEEN SUBCLONED AND SOME SUPERNATANTS CONTAIN MORE THAN ONE CLASS OF IG. THIS ALMOST CERTAINLY REPRESENTS ANTIBODIES WITH DIFFERENT SPECIFICITIES AND THESE LINES WILL DEFINITELY NEED TO BE CLONED SEVERAL TIMES, AS WILL ANY HYBRIDOMA LINE CHOSEN FOR RIGOROUS CHARACTERIZATION.
*OBTAINED FROM A DIFFERENT, BUT VERY SIMILAR IMMUNIZATION PARADIGM.
**ANTI-IDIOTYPES TO GM1.

All of the antibodies that enhanced Schwann cell migration were screened in dot blots for their ability to recognize CNS and PNS myelin. Two of the enhancing antibodies (S237E and S1211G) recognized molecules in both CNS and PNS myelin. PNS myelin may thus contain some inhibitory molecules in common with CNS myelin. The only growth inhibitory molecules characterized thus far in the nervous system are found only in the CNS myelin (Schwab et al, Mental Neurology 109:2 (1990)). Furthermore, all of the enhancing antibodies were screened for their ability to potentiate Schwann cell migration on CNS tissue substrates (i.e., optic nerve substrates). Antibody S2110B, potentiated Schwann cell migration on adult optic nerve substrates.

Many of the antibodies in Table 1 effect Schwann cell migration by binding cells and activating second messenger cascades; hence they function as agonist antibodies. In the studies described below, representative experiments used to characterize these antibodies are illustrated. Antibody 21, a migration promoting antibody, and antibody 131C, an inhibitor, i.e., an antagonist, are highlighted. However, many of the antibodies in Table 1 have the characteristics of agonist antibodies.

Figures 5A, 5B, 5C:
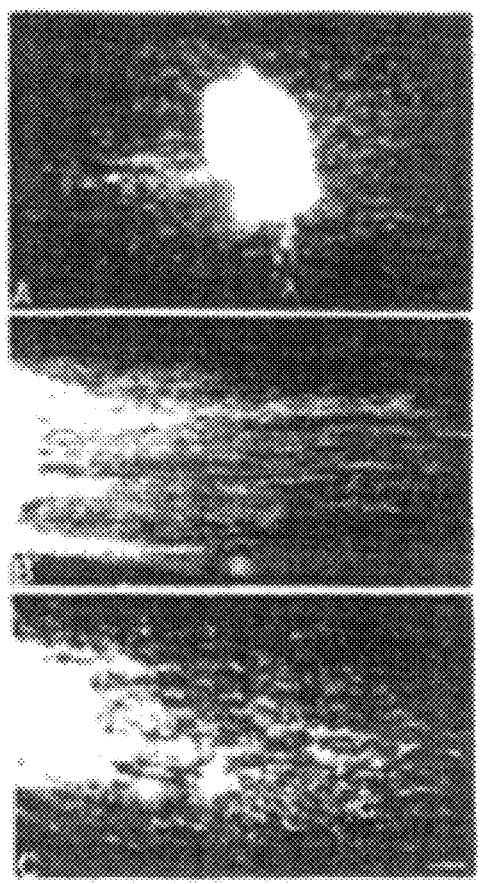
FIGS. 5A–5C: Enhancement of Schwann cell migration by antibodies 216C and 21. DRGs were explanted onto a cryostat section of normal sciatic nerve and cultured in the presence of antibodies (117E, 21, or 216C) for 72 hours. Photographs are of carboxy fluorescein labeled Schwann cells migrating out of the DRG explant on to the nerve substrate in the presence of (FIG. 5A) 117E, (FIG. 5B) 216C, and (FIG. 5C) 21 after 72 hours in culture. Scale bar=100 μm.
Figure 6A:
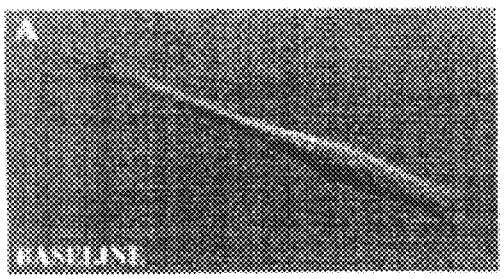
FIGS. 6A–6D: Exposure to migration-modulating antibodies leads to changes in Schwann cell shape and activity. After recording 45 minutes of baseline activity (FIGS. 6A,B), primary Schwann cell cultures were perfused with either antibody 21 or 131C. Antibody 21 led to enhanced lamellapodial activity at the bipolar ends of the Schwann cells (FIG. 6C) and increased cell movement. Only the lamellapodia that are projecting at an angle are clearly visible. Exposure to antibody 131C led to gradual withdrawal of the bipolar processes and rounding up of cells (FIG. 6D). Images in FIGS. 6C and D were taken approximately 45 minutes after antibody perfusion.
Figure 6B:
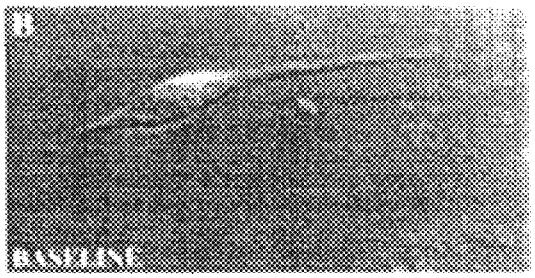
Figure 6C:
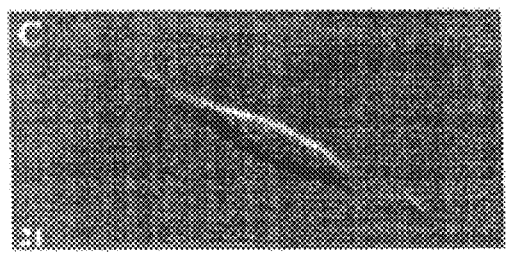
Figure 6D:
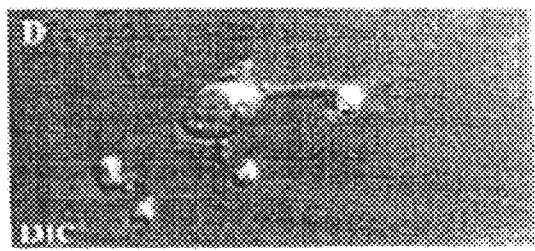
Figure 7A:
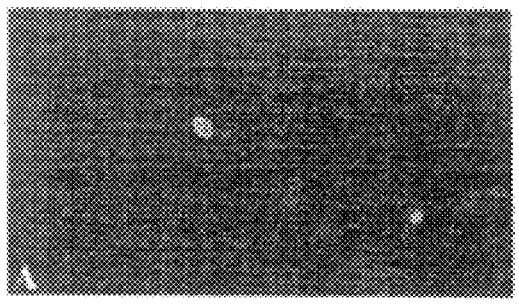
FIGS. 7A-7D: Exposure to migration-modulating antibodies leads to changes in cytosolic calcium levels. Fluo-3 loaded Schwann cells were perfused with antibodies 21 and 131C. Exposure to 21, a migration-promoting antibody, increased calcium levels (FIG. 7A-baseline, FIG. 7B-18 minutes after exposure to 21) whereas exposure to 131C, a migration-inhibitory antibody, lead to a drop in calcium levels (FIG. 7C-baseline, FIG. 7D-30 minutes after exposure to 131C). IMAGE 1 uses a color spectrum to code fluorescent signals, highest calcium is assigned red, lower concentrations are assigned violet.
Figure 7B:
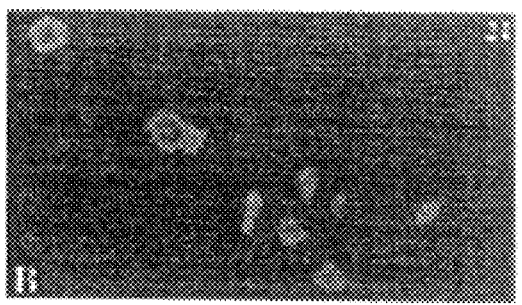
Figure 7C:
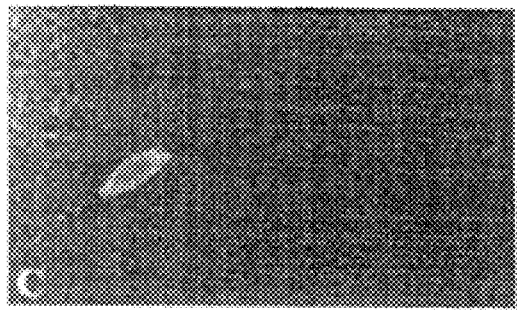
Figure 7D:
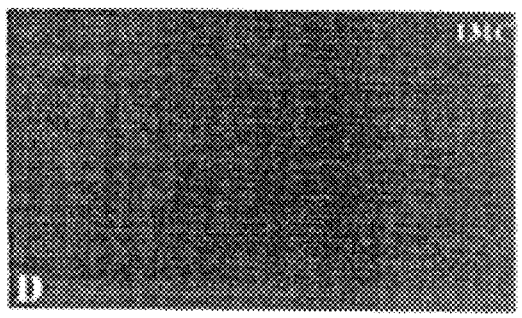

The first in vitro bioassay used to screen the panel of antibodies was an assessment of Schwann cell migration from a sensory ganglion explant onto a cryostat section of sciatic nerve. It is noteworthy that the migrating cells are definitely Schwann cells and, once committed to migration, cells do not divide. FIGS. 5A–5C illustrate two antibodies that potentiate Schwann cell migration and one antibody that recognizes a Schwann cell membrane protein but has no functional activity in this assay. The agonist antibodies cited above recognize antigens that are present on Schwann cell membranes as well as on rat sciatic nerve sections—the substrate employed in this migration bioassay. There are several ways in which these antibodies could regulate Schwann cell migration in this assay. For example, these antibodies could produce their effects by binding to Schwann cell surface molecules, including receptors and adhesion molecules, and thus modulate the cellular machinery involved in cell movement; this would be true for agonist antibodies. Alternatively, they may bind to and mask inhibitory or attractive molecules that are present on nerve substrates and thus influence Schwann cell migration by modifying the environment in which they migrate.

Many of the antibodies directly modulate Schwann cell migration by binding to their respective antigens on Schwann cell membranes. In the cryostat section assay, enhancement is dependent on the presence of antibody in the culture media. Pre-treating the nerve substrate with the concentrated antibody alone does not affect the rate of Schwann cell migration, thus indicating a direct effect of the antibody on Schwann cells. The most compelling argument is made by experiments using only plastic as a substrate for migration. In time-lapse recordings of primary Schwann cells cultured on plastic, addition of migration-promoting antibodies leads to enhanced lamellipodial activity and increased movement of Schwann cells, whereas exposure to inhibitory antibodies results in the gradual withdrawal of the bipolar leading edges and the eventual rounding of Schwann cells (FIGS. 6A–6D).

The apparent direct modulation of Schwann cell shape and motility by these antibodies is likely to involve second messenger cascades such as Ca++ level changes and protein phosphorylation. Thus, the intracellular change in calcium levels in Schwann cells was monitored following antibody exposure by using a fluorescent Ca++ indicator, Fluo 3-AM.

Method: The methods for calcium imaging are as previously described (Jahromi et al., Neuron 8:1069–1077 (1992)) for Schwann cells. Primary cultures are established on coverslips. Cells are washed in 10 mM HEPES-buffered balanced salt and the incubated with 1 ml HEPES-buffered balanced salt containing 10 $\mu$M Fluo-3 acetoxymethyl ester (AM) (Molecular Probes Inc.) and the non-ionic detergent pluronic acid F127 0.5 mg/ml. Heavy metals that might bind to Fluo-3 and interfere with its calcium sensitivity are chelated by adding 10 $\mu$M Tetrakis (2-pyridyl methyl) ethylenediamine (TPEN) to the incubation medium. Cells are loaded with dye for 2 hours at room temperature. The cultures are washed and placed onto a 37° C. stage on a Zeiss IM microscope. The chamber is then perfused at a rate of 2 ml/min with either control agents or antibodies. Images are collected every minute using the IMAGE 1 system, a SIT camera, a computer controlled shutter on the UV light source and an optical recorder. After 15 minutes of base-line recording, medium with pure agonist antibody is perfused and the fluorescent changes induced in neuronal cell somas by antibody stimulation are measured. The calculation: {(Flourescence with antibody–Fluorescence baseline)/Fluorescence baseline}, can be directly related to calcium changes. As controls, other nonfunctional antibodies are tested as is a calcium ionophore.

Exposure to antibody 21 led to 81±7% (n=9) increase in Fluo-3 fluorescence in Schwann cell soma, indicating an increase in intracellular Ca++. In contrast, exposure to antibody 131C leads to a decrease in intracellular calcium (FIGS. 7A–7D). This reduction in calcium levels precedes changes in cell shape observed in time lapse movies. The calcium increase in response to antibody 21 began approximately 10 to 15 minutes after antibody exposure and remained elevated in most of the cells for the duration of the recording (another 15 minutes). In a few cells, Ca++ levels returned to near basal levels after 7–10 Minutes. The slow rate of calcium level change suggests that it is most likely due to the release of calcium from intracellular stores rather than from extracellular Ca++ influx through channels on Schwann cell surfaces. Change in calcium precedes changes in cell motility, since in time lapse movies significant changes in motility were seen only after about 30–45 minutes exposure to antibodies.

Figure 8:
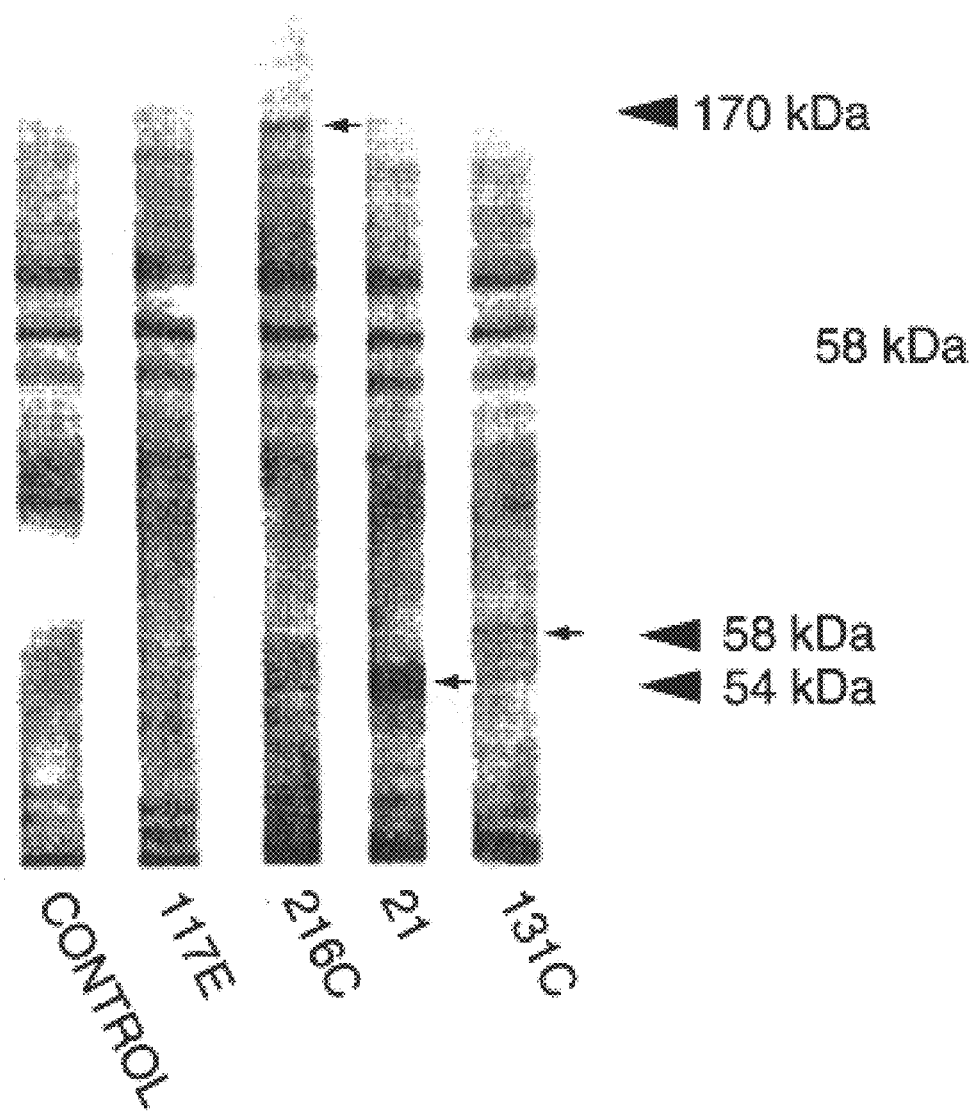
FIG. 8: Exposure to antibodies leads to tyrosine phosphorylation of Schwann cell substrates. Primary Schwann cells were cultured for 45 minutes in RPMI/10% FCS medium (control) or in medium containing antibodies (117E, 21, 131C, 216C). Schwann cells were then harvested and probed with anti-phosphotyrosine antibodies. The major protein substrates phosphorylated by the antibodies are marked with arrows. 216C, 21, and 131C induced phosphorylation of 170 kDa, 54 kDa, and 58 kDa proteins, respectively. Antibody 117E did not induce phosphorylation.

The effect of antibodies on tyrosine, serine, and threonine phosphorylation of intracellular protein substrates was analyzed. Exposure to antibody 21 resulted in tyrosine phosphorylation of 54 kD, 48 kD, and 42 kD substrates (FIG. 8, other antibodies lead to the phosphorylation of different molecular weight substrates) serine phosphorylation of 54 kD and 50 kD substrates, and threonine phosphorylation of the 54 kD substrate within 45 minutes. Antibody 131C promotes the phosphorylation of a 58 kD substrate. Some of these substrates may be proteins already known to be phosphorylated during changes in cell adhesion and motility. Candidate proteins include: 115–130 kD complex called pp130, 80/85 kD contactin, 70 kD paxillin, 69 kD laminin receptor, 68 kD neurofilament, 59 kD vimentin, 45 kD MAP kinase, 42–44 kD MAP kinase, 46 kD talin, 45 kD laminin binding protein, and 43 kD actin.

Changes in cytosolic calcium concentrations and phosphorylation of specific cellular proteins has been previously shown to influence the activity of actin-binding contractile proteins, the onset of cell migration, and the degree of cell-cell adhesion of various cell types including the precursors of Schwann cells, the neural crest cells (Forscher, Trends in Neurosci. 12:468–474 (1989); Newgreen and Gooday, J. Comp. Neurol. 259:330–347 (1985); Doherty et al, Cell 67:21–33 (1991)) and is likely to influence Schwann cell motility similarly.

The above observations indicate that binding of agonist antibodies, like 21, to their antigens on Schwann cell surfaces activates second messenger cascades such as protein phosphorylation and changes in intacellular calcium levels, leading eventually to cytoskeletal reorganization and thus changes in Schwann cell motility.

EXAMPLE III

Figure 9:
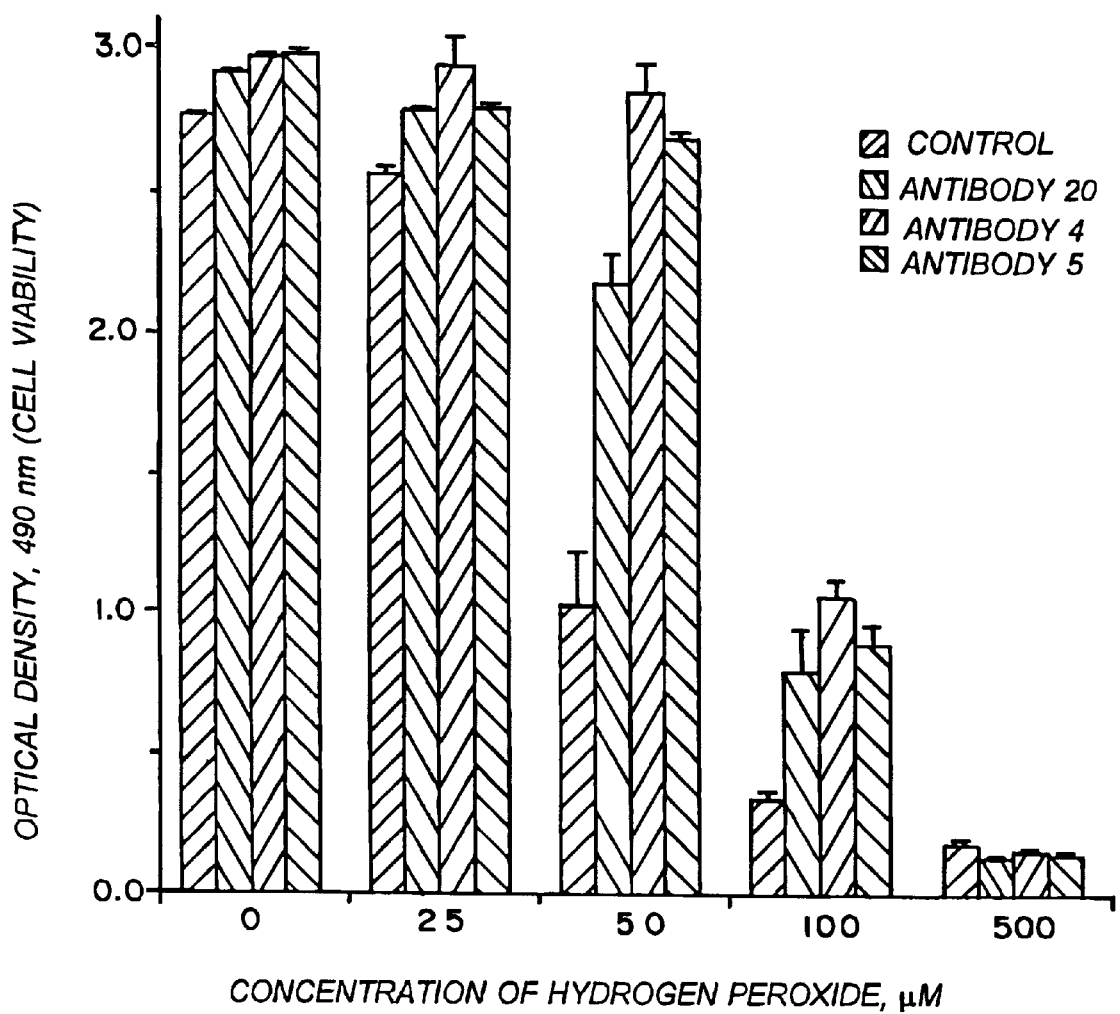
FIG. 9: GM1-agonist antibodies protect mouse Schwannoma cells against hydrogen peroxide toxicity.

GM1-Agonist Antibodies Protect Mammalian Cells Against Hydrogen Peroxide Toxicity To determine whether anti-idiotypic GM1 antibodies protect against cytotoxicity induced by hydrogen peroxide exposure, the mouse B1.1 Schwannoma cell line was preincubated in NS1 CM (control) or anti-idiotypic GM1 agonist antibody 4, 5 or 20. Following treatment with hydrogen peroxide at 0, 25 $\mu$M, 50 AM, 100 $\mu$M and 500 $\mu$M, cell viability was determined using a Promega Cell Titer 96 Aqueous cell toxicity assay (Promega Corp, 2800 Woods Hollow Road, Madison Wis. 53711). The results presented in FIG. 9 demonstrate that the antibodies protect against the toxic effects of hydrogen peroxide (optical density is a measure of the number of live cells).

Figure 10:
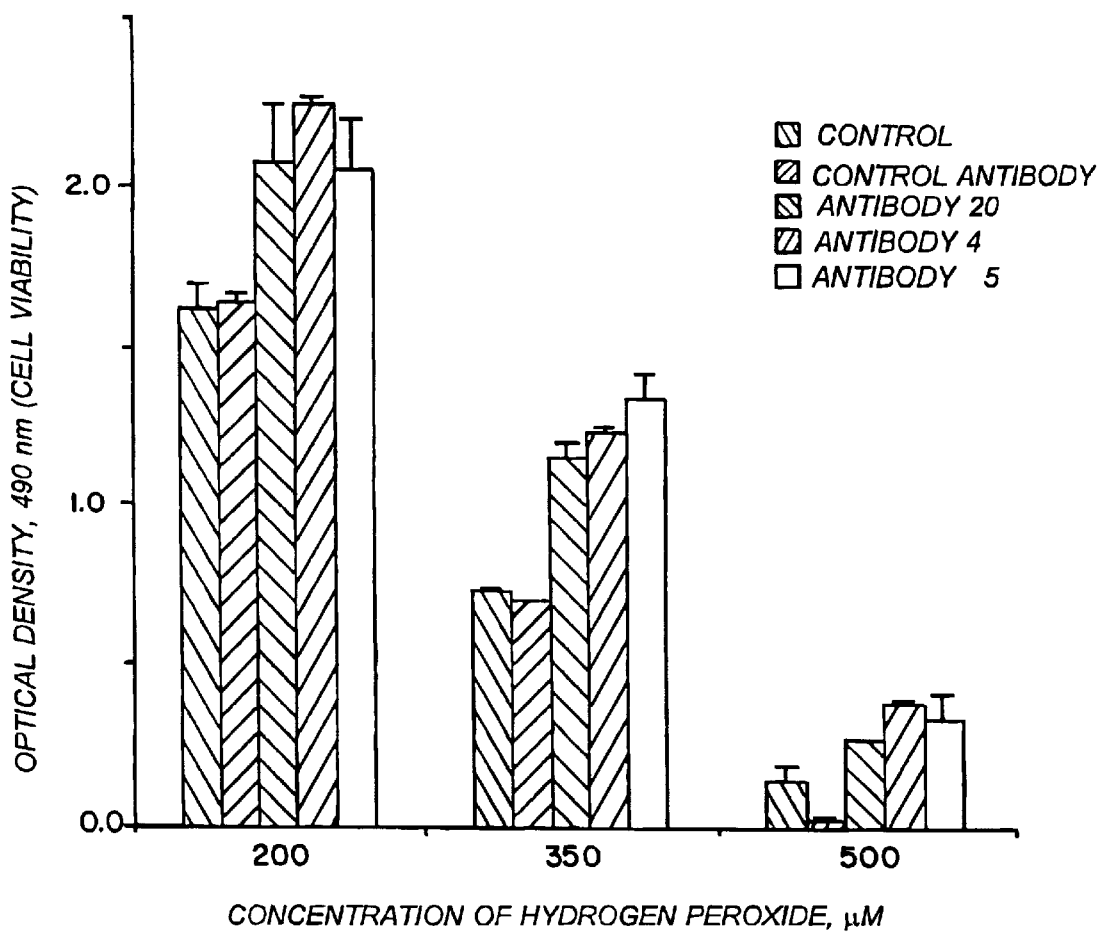
FIG. 10: GM1-agonist antibodies protect human neuroblastoma cells against hydrogen peroxide toxicity.

GM1 is known to protect against cell death following growth factor deprivation or glutamate exposure. SKNSH human neuroblastoma cells (Helson et al, Cancer Res. 35:2594 (1975); Biedler et al, J. Natl. Can. Inst. 57:683 (1976)) were preincubated in NS1 CM (control), a nonfunctional antibody of the same immunoglobulin class, or anti-idiotypic GM1 agonist antibody 4, 5 or 20. Following treatment with hydrogen peroxide at 200 $\mu$M, 350 $\mu$M or 500 $\mu$M, cell viability was determined using a Promega Cell Titer 96 Aqueous cell toxicity assay. The results presented in FIG. 10 demonstrate that the antibodies protect against the toxic effects of the hydrogen peroxide (optical density is proportional to the number of live cells).

Murine hybridomas 5-GM and 21-S were deposited with the American Type Culture Collection, 12301 Parklawn Drive, Rockville, Md. 20852 USA, under on Aug. 19, 1993 the terms of the Budapest Treaty and were assigned deposit numbers ATCC 11439 and ATCC 11440, respectively.

All documents cited hereinabove are incorporated in their entirety by reference.

While the invention has been described with respect to what is presently regarded as the most practical embodiments thereof, it will be understood by those of ordinary skill in the art that various alterations and modifications may be made which nevertheless remain within the scope of the invention as defined by the claims which follow.

What is claimed is:

1. A method of facilitating growth of a nerve cell comprising contacting said cell with an antibody, or fragment thereof that binds antigen, that mimics an agent that binds to a receptor on the surface of said cell and thereby facilitates said growth, wherein said contacting is effected under conditions such that said antibody, or said fragment, binds to said receptor and thereby facilitates said growth, wherein said antibody is produced by a hybridoma having ATCC deposit number 11439.

2. A method of facilitating growth of a nerve cell comprising contacting said cell with an antibody, or fragment thereof that binds antigen, that mimics an agent that binds to a receptor on the surface of said cell and thereby facilitates said growth, wherein said contacting is effected under conditions such that said antibody, or said fragment, binds to said receptor and thereby facilitates said growth, wherein binding of said antibody to said receptor activates protein phosphorylation.

3. The method according to claim 2 wherein said phosphorylation occurs at a tyrosine residue.

4. The method according to claim 2 wherein said phosphorylation is of a 65–75 kD or 48–52 kD substrate.

* * * * *